(12) United States Patent
Curtis et al.

(10) Patent No.: US 8,096,197 B2
(45) Date of Patent: Jan. 17, 2012

(54) AIR DISPLACEMENT LIQUID DELIVERY SYSTEM AND RELATED METHOD

(75) Inventors: Richard H. Curtis, Gorham, ME (US); David L. Bohnsack, Westbrook, ME (US); George Rodrigues, Westbrook, ME (US); Marc Boillat, Auvernier (CH)

(73) Assignee: Artel, Inc., Westbrook, ME (US)

( * ) Notice: Subject to any disclaimer, the term of this patent is extended or adjusted under 35 U.S.C. 154(b) by 1021 days.

(21) Appl. No.: 11/694,198

(22) Filed: Mar. 30, 2007

(65) Prior Publication Data

US 2007/0241130 A1 Oct. 18, 2007

Related U.S. Application Data

(60) Provisional application No. 60/788,477, filed on Mar. 31, 2006.

(51) Int. Cl.
*G01N 1/22* (2006.01)
(52) U.S. Cl. .................................... 73/863.12
(58) Field of Classification Search ............... 73/863.12, 73/864.01, 864.11; 222/1, 52, 59, 71, 596
See application file for complete search history.

(56) References Cited

U.S. PATENT DOCUMENTS

| | | | |
|---|---|---|---|
| 5,895,838 A | 4/1999 | Harjunmaa | |
| 6,662,122 B2 | 12/2003 | Salje | |
| 7,146,867 B2 | 12/2006 | Jagdhuber | |
| 2002/0168297 A1 | 11/2002 | Shvets et al. | |
| 2007/0204930 A1* | 9/2007 | Phallen et al. | 141/83 |

FOREIGN PATENT DOCUMENTS

| | | |
|---|---|---|
| EP | 1614468 | 1/2006 |
| FR | 2862888 | 6/2005 |
| FR | 2862889 | 6/2005 |

OTHER PUBLICATIONS

Notification of Transmittal of the International Search Report and the Written Opinion of the International Searching Authority, Jul. 3, 2008, 6 pp.

* cited by examiner

*Primary Examiner* — Hezron E Williams
*Assistant Examiner* — Tamiko D Bellamy
(74) *Attorney, Agent, or Firm* — Verrill Dana, LLP; Chris A. Caseiro (57) ABSTRACT

An air displacement liquid delivery system including a liquid delivery device, one or more sensors, a control unit, and a preprogrammable computing device, and a method for using the air displacement liquid delivery system. The one or more sensors are capable of obtaining information regarding conditions within and external to the liquid delivery device and sending this information to the control unit and/or the computing device. In turn, the control unit and/or computing device are capable of using this information to calculate one or more properties of gas contained within, and the air external to, the liquid delivery device, and one or more properties of a liquid that is to be aspirated or dispensed by the liquid delivery device. The system may optimally control the performance of the liquid delivery device based upon any one or more of these calculated properties.

22 Claims, 7 Drawing Sheets

AIR DISPLACEMENT LIQUID DELIVERY SYSTEM AND RELATED METHOD

CROSS REFERENCE TO RELATED APPLICATION

The present application claims the priority benefit of U.S. provisional patent application Ser. No. 60/788,477, filed Mar. 31, 2006, entitled "AIR DISPLACEMENT LIQUID DELIVERY DEVICE" of the same named inventors. The entire contents of that prior application are incorporated herein by reference.

BACKGROUND OF THE INVENTION

1. Field of the Invention

The present invention relates to liquid delivery devices. More particularly, the present invention relates to air displacement liquid delivery systems that include a liquid delivery device. Even more particularly, the present invention relates to air displacement liquid delivery systems that use air to separate liquid aspirated by the liquid delivery device from one or more components of that liquid delivery device. Still more particularly, the present invention relates to air displacement liquid delivery systems that sense information regarding conditions within and external to a liquid delivery device of the system and that use this information to control liquid displacement by that liquid delivery device. Still more particularly, the present invention relates to methods of using the liquid delivery systems of the present invention.

2. Description of the Prior Art

Figure 1:
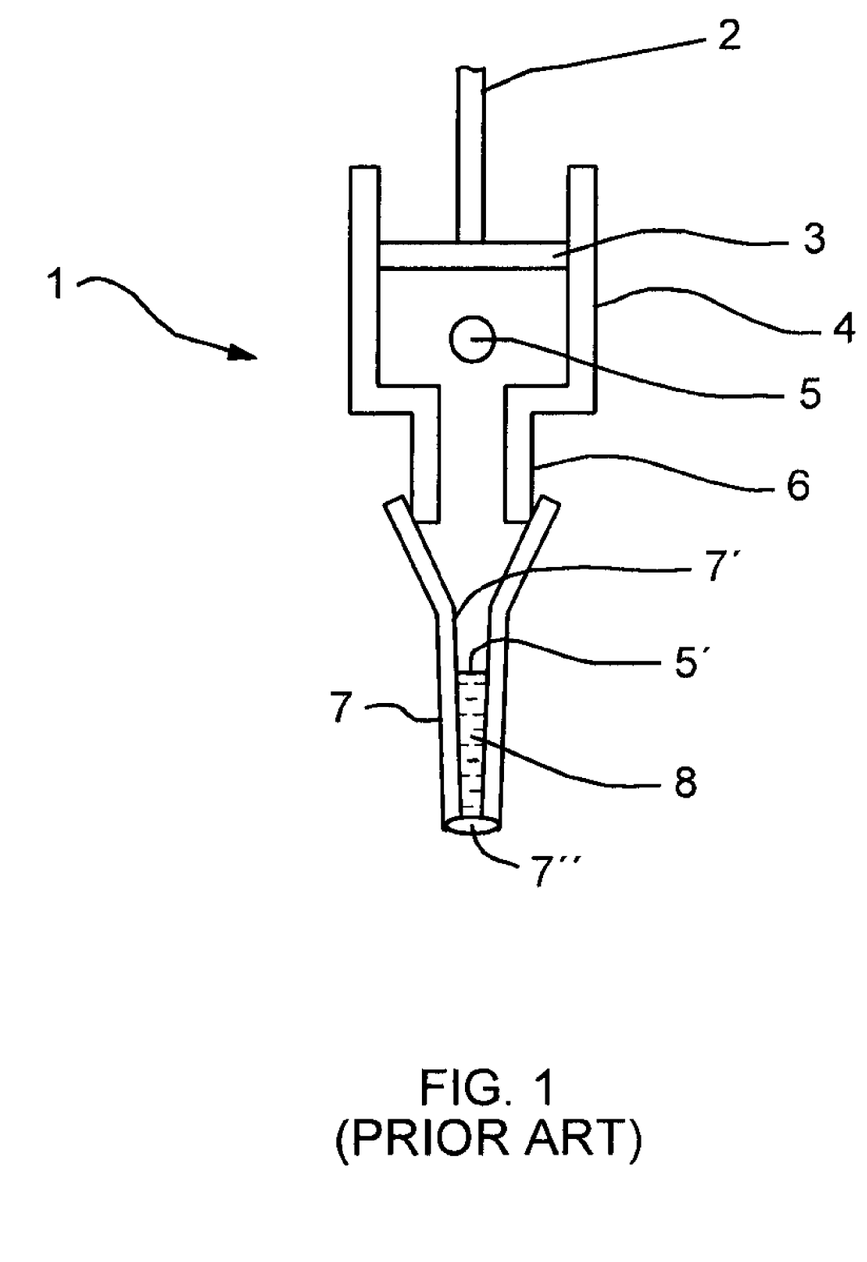
FIG. 1 is a side cross-sectional view of a prior manual air displacement liquid delivery device.

Present air displacement liquid delivery devices, such as, for example, the device described in PCT Patent Application PCT/US04/03824, which is incorporated herein by reference in its entirety, may be manual or they may be automated. Present manual air displacement liquid delivery devices are configured in the same general way. Referring to FIG. 1, the basic elements of an example manual air displacement liquid delivery device 1 are a piston 2 having a plunger 3 movable within a cylinder 4 which causes air (or other gas), represented by molecule 5, to be displaced along a shaft 6 and into a tip 7, which is able to hold a liquid 8 for delivery of that liquid 8. The point at which the air 5 and liquid 8 meet in the tip 7 is identified herein as interface 5'.

Manual air displacement liquid delivery devices, such as device 1, typically use the air 5 to separate the liquid 8 being delivered from the tip 7 from contacting the shaft 6, the cylinder 4, the plunger 3, the piston 2 and other rigid components of these devices 1. The air 5 therefore serves to prevent contamination and degradation of the delivery device 1 itself, and to prevent contamination of any liquids 8 that are to be aspirated into or delivered from the device 1.

Figure 2:
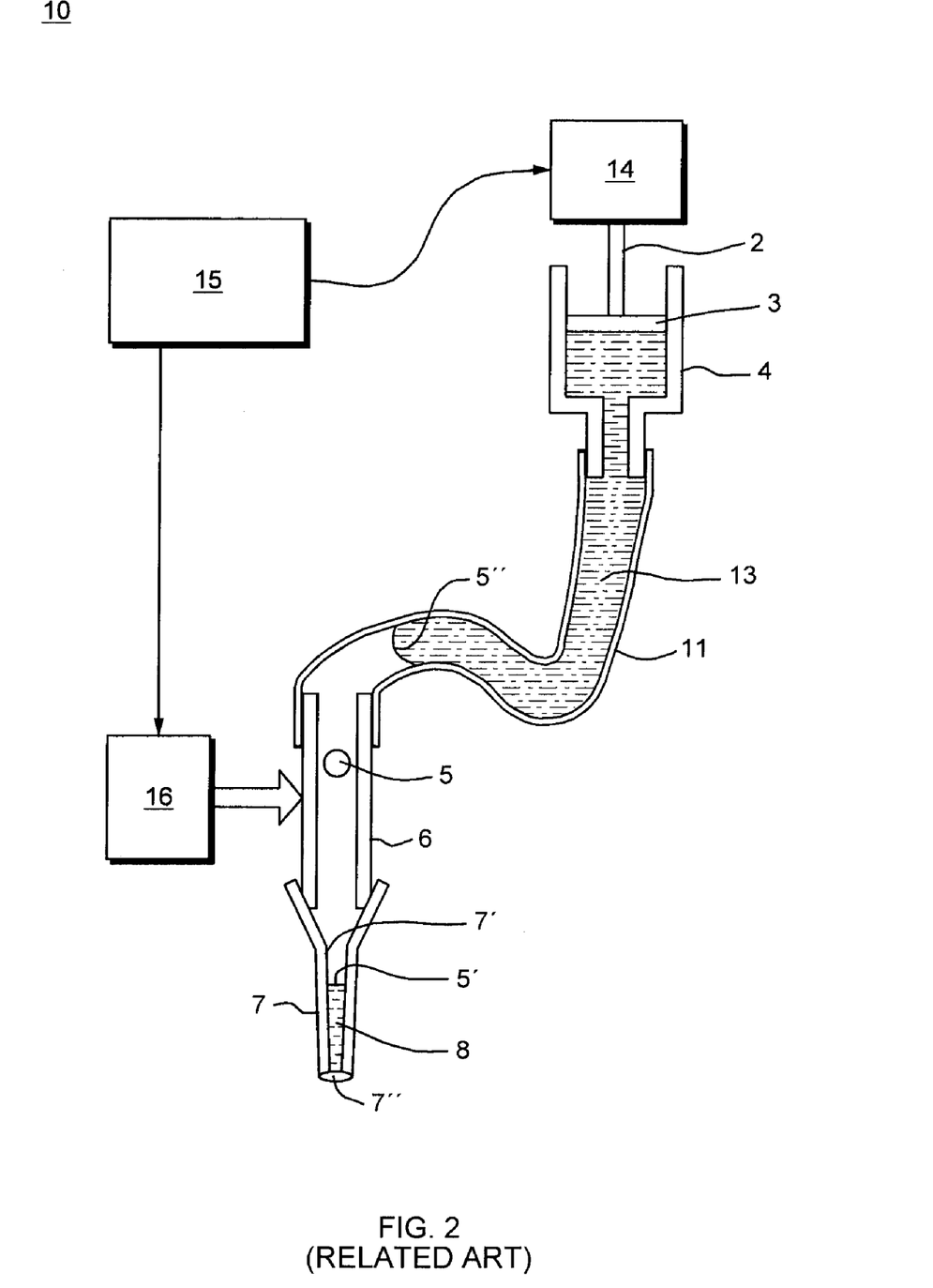
FIG. 2 is a side view of a related automated air displacement liquid delivery device, showing some of the components of the device in cross-section.

Present automated air displacement liquid delivery devices are configured somewhat differently than are existing manual devices 1. An example of an automated air displacement liquid delivery device is shown in FIG. 2. Automated air displacement liquid delivery device 10 includes the piston 2 having the plunger 3 movable within the cylinder 4. When the piston 2 is moved, air 5 is displaced within flexible tubing 11, within the shaft 6, which is connected to the tubing 11, and within the tip 7. The cylinder 4 and tubing 11 of these automated devices 10 includes a "working fluid" 13 which creates a second air interface 5" that helps ensure separation of the liquid 8 contained in the tip 7 and the working fluid 13. Further, the piston 2 of the device 10 is actuated with an actuator 14, which in turn is under control of a control unit 15.

The device 10 also may include a second actuator 16 used to move the tip 7 to and from vessels for aspiration and dispensation.

When the tip 7 of either type of liquid delivery device is inserted into a source vessel containing a liquid, the liquid seals the opening of the tip 7. When this happens, the mass of the air 5 trapped inside the tip 7 cannot change, except due to evaporation of the liquid. During aspiration, when the liquid 8 enters the tip 7, it will begin to evaporate unless the air 5 above the liquid 8 is already saturated with the vapor. Heat will also be transferred into or away from the air 5 if it is at a different temperature than that of the liquid 8 or the delivery device 1 or delivery device 10. Once the tip 7 is removed from the source vessel, surface tension may hold liquid 8 within the tip 7 even if the gas pressure at the air interface 5' changes slightly due to continuing evaporation or changing temperature. If surface tension is low due to the type of liquid 8 being aspirated, or if the pressure change in the air interface 5' is great enough, then liquid 8 may come back out of the tip 7 as it is moved from the source vessel to a receiving vessel, for example.

Further, liquid 8 evaporates from the interface 5' inside the tip 7 during the aspiration process and any subsequent pause that may occur before the tip 7 is removed from the liquid in the source vessel. According to the ideal gas law, the number of moles of air 5 trapped in the space above the liquid 8 increases due to that evaporation. Thus, the volume of liquid 8 drawn up into the tip 7 is less than would be expected based on the volume of air 5 displaced by movement of the plunger 3. The size of the discrepancy depends on a number of factors; among them are the length of time that the tip 7 remains immersed in liquid contained in the source vessel during aspiration and the vapor pressure of the liquid 8. In the case of liquids with very high vapor pressure (e.g., methanol), the error due to evaporation can be substantial. In these cases, the faster that the tip 7 is withdrawn from the source vessel, the less evaporation can influence the amount of liquid aspirated.

When the delivery device is being calibrated with water as the liquid, it is recommended in International Organization for Standardization (ISO) document ISO 8655, part 6, that it be preconditioned by aspirating and dispensing to waste five aliquots of liquid with the same tip to precondition (humidify) the air (within the shaft or conduit), and it is further recommended that the tip then be replaced, with the liquid then being aspirated and dispensed to waste once more. Further, according to Annex B of ISO 8655, part 2, an error of up to 2% can be incurred if the device is inadequately pre-conditioned (assuming the liquid 8 being delivered is water). Unfortunately, the preconditioning process is time-consuming, and therefore few users of these devices actually follow this procedure for routine liquid deliveries.

The process of preconditioning the device to increase humidity carries with it a liability if the liquid is at a different temperature than the air 5 at the interface 5'. If the aspirated liquid is at a different temperature than the air 5 at the interface 5', heat will be transferred between the liquid and the air, thereby changing the temperature of the air. (Heat transfer can also take place between the material of one or more components of the device and the air 5 at the interface 5'.) According to the ideal gas law, which states that the volume of a gas (air) is dependent upon its temperature, the volume of liquid aspirated into the tip therefore will be varied when such a change in temperature of the air occurs. This error becomes increasingly greater the longer that the device, including the tip, and the air in the device are exposed to the liquid at the different temperature. Thus, preconditioning of these devises can introduce error due to heat transfer if the liquid has even a slightly different temperature than the device. According to Annex B of ISO 8655 part 2, the possible error due to temperature variations is given as 0.3% per °C.

For existing liquid delivery devices, liquid entering the tip during aspiration has momentum that keeps it from stopping instantaneously when the plunger stops. Therefore, the liquid keeps flowing for a short time after the plunger stops, thereby compressing the air 5 at the interface 5'. This compression is followed by a rebound of the liquid which causes liquid to be expelled from the tip. After a period of oscillation, equilibrium is established. The magnitude of the oscillation and time it takes it to subside are dependent on the design of the device, including the design of the tip. (Generally, this is a more significant issue for larger volumes, e.g., 1000 μL, and liquids with low viscosity.) The tip should remain immersed in the source vessel during this oscillation period to get the most accurate aspiration of liquid.

Figure 3:
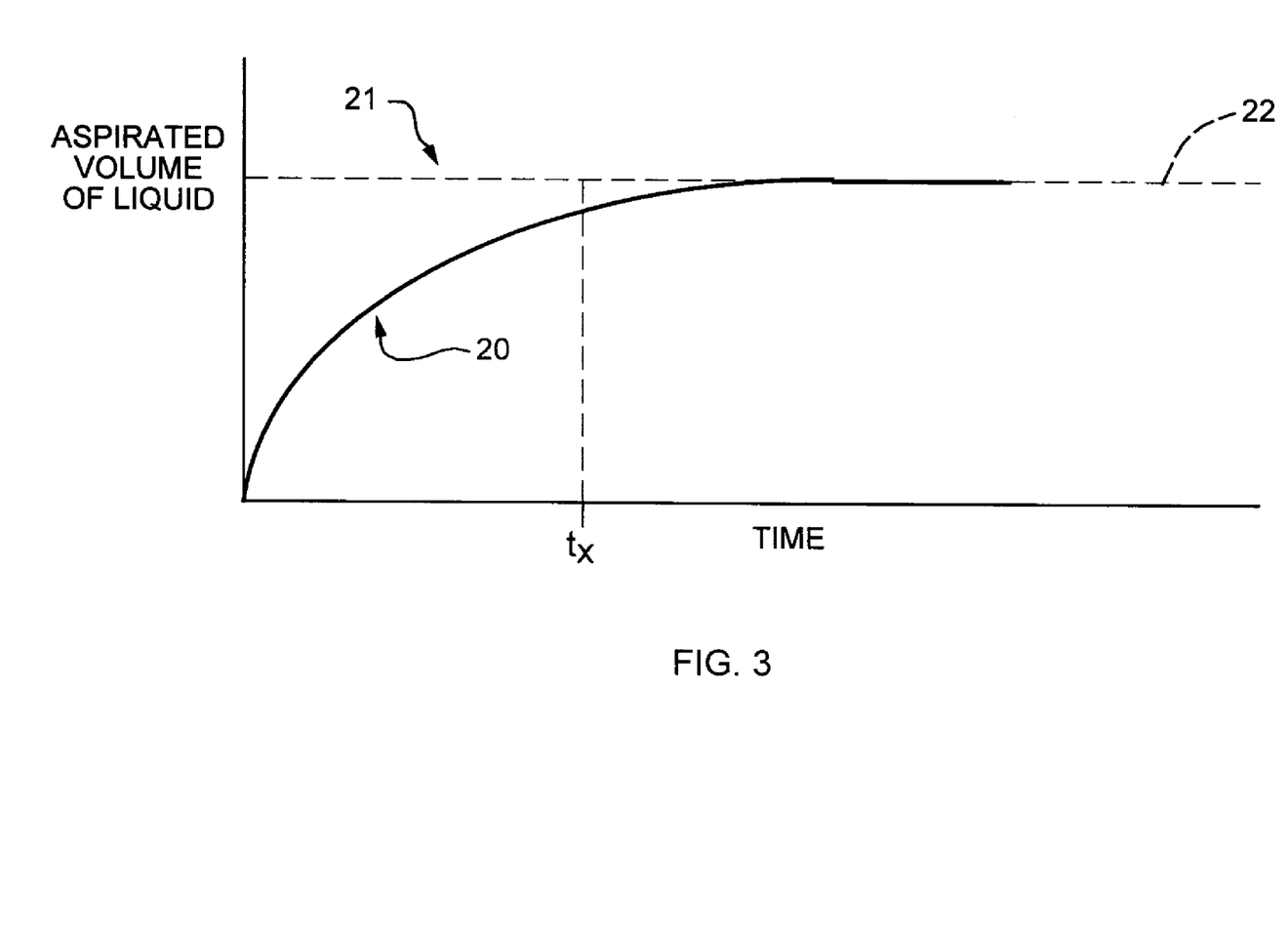
FIG. 3 is a graph showing a change in volume of a liquid actually aspirated by using a prior air displacement liquid delivery device compared to the desired volume, over time.

The liquid being aspirated or dispensed enters or exits the tip over a period of time, with the duration of that time depending on the viscosity of the liquid. During the time that the liquid is flowing into the tip, the pressure at the interface 5' is changing toward equilibrium; when equilibrium is achieved, the flow ceases. The flow rate slows as the tip fills due to a decrease in the differential pressure driving the flow. FIG. 3 is a graph of actual aspirated volume of anhydrous glycerol versus time in an application using a previously configured liquid delivery device. The actual aspirated volume 20 of the anhydrous glycerol approaches the final, desired volume 21 (to which the device was calibrated to aspirate) exponentially as endpoint 22 is approached. For a liquid with low viscosity, such as water, the delay before the desired volume is aspirated may not be noticeable by the operator. For liquids with higher viscosity, such as glycerol, serum, plasma, or polyethylene glycol, the delay can be appreciable (many seconds). If the tip is withdrawn from the source vessel prematurely, such as at time $t_x$, then the desired volume of liquid will not be aspirated, which means that an error in the amount of liquid subsequently delivered will occur. (Moreover, if the tip is left immersed in the source vessel longer than is necessary, an error in the amount of liquid aspirated will occur due to excessive evaporation and heat transfer.)

As a more specific illustration of this problem, a typical manual 100 μL air displacement delivery device (e.g., an Eppendorf 100 μL Research Pipette, which is commercially available from Eppendorf AG of Hamburg, Germany) requires 33 seconds to fully aspirate a 100 μL sample of anhydrous glycerol at room temperature. By the time 20 seconds have elapsed during this period, liquid flows so slowly into the tip, as judged by the location of the interface in the tip, that it is difficult to know when the aspiration is complete. Thirty-three seconds is a long time to wait, especially when the device is to be carefully held poised over the source vessel and the tip immersed to the correct depth (2-3 mm) for that entire time. Therefore, a busy operator often will cut that wait short by withdrawing the tip prematurely, which in turn will cause errors in liquid dispensation. Further exacerbating this problem, it often is very difficult for an operator to know how long to hold the tip within the source vessel, since this will depend on the viscosity of the particular liquid being aspirated.

It is often considered good practice for the operator to adjust the aspiration speed of a device based upon the viscosity of the liquid being aspirated. Most electronic devices are provided with a control capability for the operator to set the desired aspiration speed. It is, however, difficult for an operator to know the best speed for a given sample of liquid. For instance, there is wide variation in the viscosity of serum samples; an operator can hardly be expected to determine the best aspiration speed for each sample. Therefore, an operator who is about to aspirate a particular serum is more likely to set a value that he/she thinks may be adequate for that serum type and hope for the best. In doing so, he/she may be aspirate different volumes among samples due to the sources of error already described.

Further, due to surface properties of the aspirated liquid, movement of the piston of these devices will not cause the interface meniscus to move immediately. If no liquid is in the tip, a certain negative pressure of air 5 at the interface 5' is required to overcome the surface tension of the liquid and draw it into the tip. Thus, in this case, no liquid is drawn into the tip while the surface tension is being overcome. This failure to initially aspirate any liquid causes a small error in the amount of liquid aspirated by the device. For an existing device, this error is accounted for whenever the device is sent for calibration. For these devices, it turns out that so long as the type of liquid aspirated during use is the same as the type of liquid aspirated during this calibration process, which is rarely the case, the error is adequately compensated. If, however, the device is used to deliver liquid having a different surface tension than the liquid aspirated in the calibration process, which is often the case, then the correction introduced during calibration will not be correct, and therefore an error in delivery volume will result.

Likewise, when dispensing liquid from the tip, the first motion of the piston creates a slight overpressure of air 5 at the interface 5', yet results in no motion of the interface meniscus. This is true because the contact angle between the liquid and an inner wall of the tip changes as pressure is applied, and this in turn causes a change in the shape of the interface meniscus without causing the point of contact between liquid and inner wall of the tip to move. This will be true for any liquid-solid interface for which the leading contact angle is greater than the trailing contact angle. It is a stick-slip phenomenon. When the overpressure becomes great enough, the interface meniscus will start to move along the inner wall of the tip. Additionally, if the tip is held in ambient air as liquid is dispensed, then surface tension of the liquid will tend to cause liquid to be held in the tip until enough overpressure is created to overcome the forces of surface tension and stick-slip at open end 7' of FIGS. 1 and 2 of the tip, thereby allowing the liquid to exit the tip. In the instance that all of the liquid in the tip is being dispensed at once, these effects are irrelevant. It is only necessary to produce enough piston motion to dispense all of the liquid, including providing a "blowout" through the tip opening 7' to expel the final droplet of liquid. In the instance that multiple dispense operations are to be performed following a single aspiration, it is desirable that the volume of each dispense be the same. Very commonly, in practice, the first such dispense will be a different volume than the others, and, for that reason, should be discarded.

As liquid is aspirated into the tip, a negative pressure is required within the tip to hold the interface meniscus above the level of the liquid in the source vessel because of the force of gravity on the liquid in the tip. This pressure is usually called the "head pressure", and it is dependent on the density of the liquid aspirated. Usually, when the device is sent for calibration, the effect of this head pressure is corrected. If, however, the density of the liquid used to calibrate the device is different than the density of the liquid being delivered in another operation of the device, an error in delivered volume due to liquid density will be seen. According to ISO 8655 part 2, Appendix A, the magnitude of such error can be up to 1%.

Another application of the liquid delivery device is to use it in a titration procedure, in which the operator adds one liquid to another in small increments, while observing by eye or instrument the process of a reaction. For instance, the acidity of a sample of liquid can be determined by adding a base of known concentration and an indicator dye. In these applications, the base is added in small aliquots while stirring the liquids together and observing the color of the solution. When pH reaches a particular value, the dye changes color, signaling the operator to stop adding basic solution. It often is desirable to know the volume of base that was added to change the pH to that point. Using a device such as shown in FIGS. 1 and 2, the volume of liquid added is dependent on the density and surface properties of the liquid, as explained above. Calibration of the device with water does not provide the proper correction when the device is actually used to dispense another liquid type.

As might be expected, the best reproducibility of results from using a liquid delivery device is obtained when the pause between the end of aspiration and the removal of the tip from the source vessel is not too short or not too long. This can be determined by experimentation and experience for a device of a particular size or design, as well as based upon the type of liquid to be aspirated. A several second pause is generally recommended for aqueous solutions; however this is a generalization that may not be optimal for all situations.

When aspirating liquids with high vapor pressure, the error created due to heat transfer between the liquid and the interface is likely to be much less than the error due to evaporation of the liquid. For this reason, it is generally best to precondition the tip and rest of the device very thoroughly, by saturating the air interface with vapor from the liquid, before quantitatively aspirating the liquid. It is nonetheless difficult for a user to know to what extent the tip and rest of the device must be preconditioned to avoid error. In these instances, the operator must balance the need to precondition the device versus time. Since operators often will err on the side of over preconditioning the device, much time can be needlessly wasted.

In the instance of existing automated liquid delivery devices 10 that are pre-programmed to follow a certain sequence, a given aspiration protocol may be optimal for one volume or liquid sample, but not for another. The person creating the protocol must experiment to determine the correct aspiration speed and pause interval, as well as the correct dispense speed and pause interval. Considerable time and expertise are required to find the best parameters to optimize the accuracy and precision of results.

In light of the above mentioned limitations of the existing air displacement delivery devices, what is needed, therefore, is an air displacement delivery system that is capable of optimizing its own performance based on one or more properties that it determines regarding the air contained within the apparatus, the ambient air surrounding the apparatus, and/or the type of liquid to be aspirated and/or dispensed. The needed system should minimize the length of time that its tip is immersed in a source vessel, and which minimizes the need to precondition its tip to attain accurate results. The needed system also should minimize oscillation by avoiding abrupt flow transitions by tapering off the flow of liquid at the end of aspiration, and should be able to detect the end of oscillation and determine when it is the best time to withdraw the tip from a source vessel. The needed system further should shorten the amount of time a tip must be held within a liquid sample after aspiration. Even further, the needed system should be able to determine viscosity of an aspirated liquid sample, and based on this viscosity value, dispense the most accurate and reproducible delivery volume in the least amount of time. Still further, the needed system should be able to determine the actual volume of an aspirated liquid aliquot, regardless of any surface tension between the system and the liquid sample from which the liquid aliquot is being aspirated. Still further, the needed system should be able to determine the actual volume of a liquid that is dispensed from the system during any given dispensation, regardless of any surface tension between the system and the surface of the liquid into which the system is to dispense or contact angles of that liquid. Still further, the needed system should be able to deliver a precise volume of a liquid independent of the actual density of that liquid. Still further, the needed system should be able to determine optimum pause time, i.e., the time between the end of aspiration and the removal of the tip from a liquid sample after aspiration. Still further, the needed system should be able to use information specific to the nature of the liquid to be dispensed for the purpose of minimizing dispensation error and dispense time.

SUMMARY OF THE INVENTION

The present invention is an air displacement liquid delivery system for the aspiration of a liquid aliquot from a liquid source and dispensation of the aliquot. The system includes a computing device, a control unit, an ambient control device, one or more condition sensors and a liquid delivery device. The liquid delivery device includes an actuator, a piston having a plunger, a cylinder having a shaft, and one or more sensors located within the shaft. The actuator effects movement of the piston and plunger within the cylinder. The liquid delivery device also includes a removable tip for holding a liquid aliquot therein. The system also includes at least one user interface to enable a user to observe information about the liquid delivery device, to control operation of the actuator, or a combination of the two. The computing device, the control unit, or both may include a user interface. The liquid delivery device includes a volume between the plunger and inner walls of the cylinder and shaft, and bounded on the bottom by the liquid being aspirated. The space contains a gas, which may be air.

The one or more sensors in the shaft are in communication with the control unit and are capable of obtaining information that may be used by other components of the system to determine one or more properties of the gas, such as information that may be used to determine the temperature, mass, pressure and/or flow rate of the gas, in this space, and transmitting that information to the control unit. Further, this information obtained by the one or more sensors and transmitted to the control unit may be used to determine one or more properties of any liquid contained in the tip, such as the viscosity or temperature of that liquid.

In addition to being in communication with the one or more sensors, the control unit is in two-way communication with the actuator. The control unit therefore is capable of receiving information from the one or more sensors and then using that information in calculating one or more properties of the gas and/or liquid in the tip. Based on these one or more determined properties, the control unit is capable of directing the actuator to optimally control the movement of the piston within the cylinder. Based on these one or more determined properties, the control unit also may cause a signal to be transmitted indicating the optimal time for removal of the tip from a source liquid after aspiration of an aliquot from that source liquid has occurred. This signal may be transmitted to an operator of the present invention for manual removal of the tip, or it may be transmitted to the actuator for automated removal of the tip.

The control unit is optionally in two-way communication with the computing device. The computing device, which may be pre-programmed to compute one or more algorithms, may receive, directly or indirectly, information obtained by the one or more sensors in the shaft. The computing device then may use that information to calculate the one or more properties of the gas and/or liquid in the tip. Based on these one or more calculated properties, the computing device is capable of directing the control unit to direct the actuator to optimally control the movement of the piston within the cylinder. Based on these one or more determined properties, the computing device also may cause a signal to be transmitted indicating the optimal time for removal of the tip from a source liquid after aspiration of an aliquot from that source liquid has occurred. This signal may be transmitted to an operator of the present invention for manual removal of the tip, or it may be transmitted to the actuator for automated removal of the tip.

The ambient condition device is in communication with the control unit, and may be used to obtain information to determine one or more properties of the ambient conditions outside the liquid delivery device, such as the temperature, pressure, and relative humidity of the ambient air, for example. Based on these one or more determined ambient condition properties, the control unit, and/or the computing device via the control unit, is capable of directing the actuator to optimally control the movement of the piston within the cylinder. Based on these one or more determined properties, the control unit, and/or the computing device via the control unit, may cause a signal to be transmitted indicating the optimal time for removal of the tip from a source liquid after aspiration of an aliquot from that source liquid has occurred. This signal may be transmitted to an operator of the present invention for manual removal of the tip, or it may be transmitted to the actuator for automated removal of the tip.

The system may be fully or partially automated. The user interfaces may be used to display information regarding performance of the apparatus, properties of the gas within the liquid delivery device and/or ambient conditions to an operator of the apparatus. The operator may then use this information to optimize the performance of the apparatus.

The present invention includes a method for optimizing the operation of a liquid delivery device in aspirating or dispensing a liquid. The method for optimizing the operation of a liquid delivery device in aspirating or dispensing a liquid may include one or more of the steps of: (1) sensing one or more conditions within the liquid delivery device; (2) sensing one or more conditions outside the liquid delivery device; (3) calculating a rate of aspiration or dispensation of the liquid based on the sensed conditions inside and outside the liquid delivery device; and (4) regulating the aspiration or dispensation of the liquid based on the calculated rate. Further, the conditions sensed within the liquid delivery device may include temperature and pressure, and the conditions sensed outside the liquid delivery device may include relative humidity and temperature of the ambient air and the temperature of the liquid source from which the liquid is to be aspirated. Even further, the step of calculating the rate of aspiration of the liquid may include the step of calculating the rate of removal of the liquid delivery device from a liquid source, and also may include the step of generating a signal to initiate removal of the liquid delivery device from the liquid source at the optimal removal time. When included, the signal to initiate removal of the liquid delivery device from the liquid source at the optimal removal time may be transmitted to an operator of the present system or it may be transmitted to the control unit. When the signal is transmitted to the control unit, the control unit may initiate the automated removal of the liquid delivery device from the liquid source. Still further, the method may include the steps of including in the calculation of the rate of aspiration or dispensation one or more characteristics of the liquid, and establishing a protocol for aspiration or dispensation of the liquid based on the one or more characteristics, and the one or more conditions on the inside and the outside of the liquid delivery device.

The present invention further provides a method for optimizing the operation of a liquid delivery device in aspirating a liquid from a liquid source. The method includes the steps of: (1) sensing one or more conditions within the liquid delivery device; (2) calculating an optimal time to remove the liquid delivery device from the liquid source based on the sensed information inside the liquid delivery device; and (3) generating a signal to initiate removal of the liquid delivery device from the liquid source at the optimal removal time. When the step of generating the signal to initiate removal of the liquid delivery device from the liquid source at the optimal removal time is performed, the signal may be transmitted to an operator of the system or it may be transmitted to the control unit. When the signal is transmitted to the control unit, the control unit may initiate the automated removal of the liquid delivery device from the liquid source. Even further, the method for optimizing the operation of the liquid delivery device in aspirating a liquid from a liquid source may include one or more of the steps of: (1) including in the calculation of the optimal removal time one or more properties of the liquid, wherein the one or more of properties of the liquid may include viscosity, vapor pressure, density, contact angle between the liquid and the material of the tip, and/or surface tension of the liquid; and (2) establishing a protocol for aspiration of the liquid based on the one or more characteristics, and the one or more conditions on the inside of the liquid delivery device. Still further, the method for optimizing the operation of a liquid delivery device in aspirating the liquid may include one or more of the steps of: (1) sensing one or more conditions outside the liquid delivery device, such as, for example, the temperature of the liquid source; and (2) including in the calculation of the optimal removal time the sensed conditions outside the These and other features and advantages of the invention will be apparent upon review of the following detailed description, appended drawings and accompanying claims.

DETAILED DESCRIPTION OF THE PREFERRED EMBODIMENTS OF THE INVENTION

Figure 4:
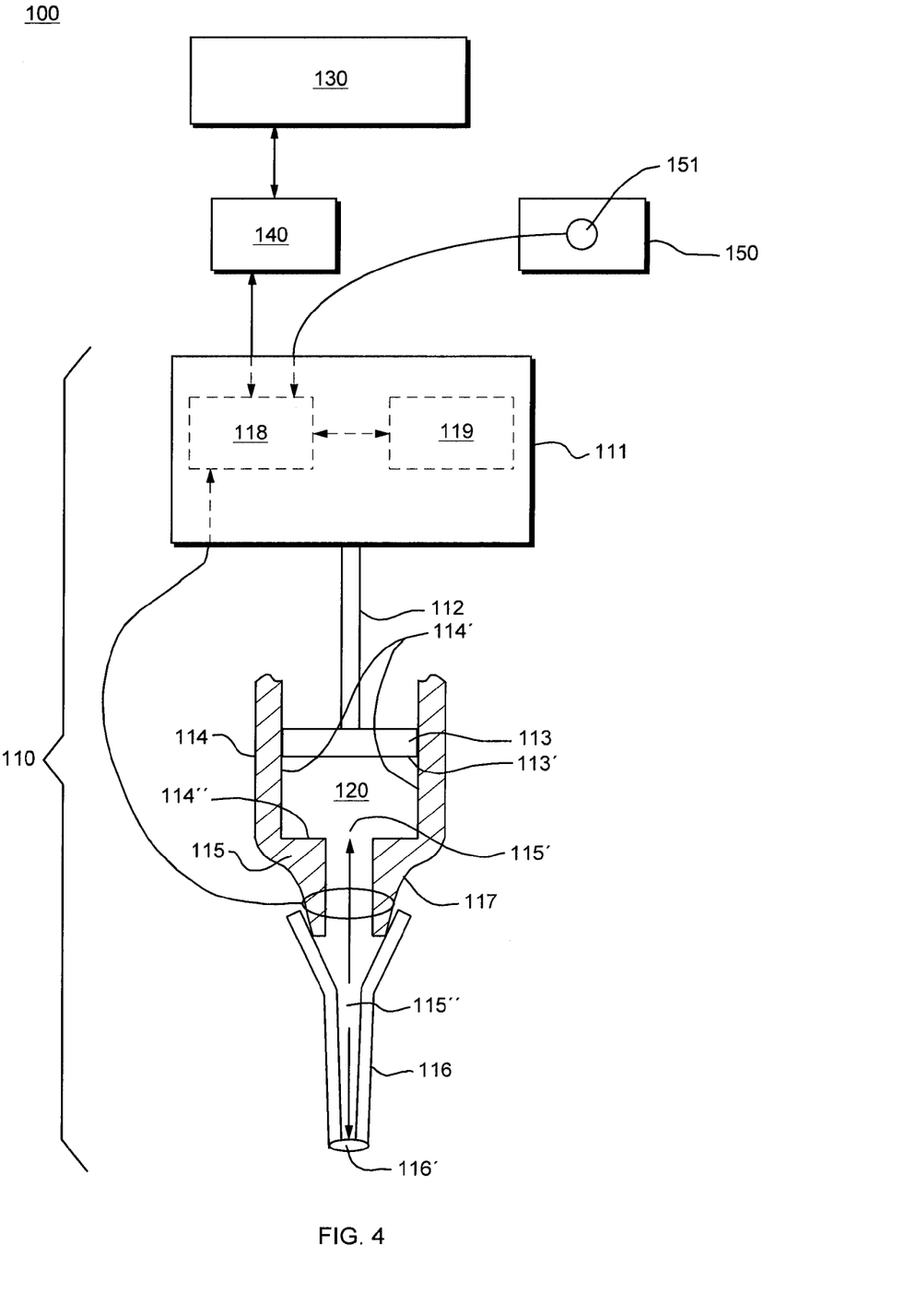
FIG. 4 is an air displacement liquid delivery system of the present invention.

The present invention is an air displacement liquid delivery system. As shown in FIG. 4, the air displacement liquid delivery system 100 includes a liquid delivery device 110. The liquid delivery device 110 includes an actuator 111 connectable to a piston 112 having a plunger 113, the piston 112 being housed within a cylinder 114 having a shaft 115 to which a tip 116 is reversibly connectable. The tip 116 is washable, and therefore reusable, or it is disposable. To help ensure that any liquid contained in the tip 116 is expelled from the tip 116, the tip 116 may be made from any one of a variety of hydrophobic materials. Those of ordinary skill in the art would recognize all of the hydrophobic materials from which the tip 116 may be formed.

Further, one or more internal sensors 117 are contained within the shaft 115. An exemplary internal sensor 117 is the Model MMCA-0001 Miniature High Speed Flow Sensor available from Seyonic SA of Neuchatel, Switzerland, which detects gas pressure and temperature within the shaft 115. Other suitable internal sensors may be used as is known by those of ordinary skill in the art A gas or mixture of gases, such as air, for example, is containable within space 120 of the liquid delivery device 110. Space 120 is specifically defined as being the region of the liquid delivery device 110 bounded on one side by lower surface 113' of the plunger 113, on two sides by inner side walls 114', and partially by inner lower wall 114" of the cylinder 114. Space 120 further includes all of conduit 115", which is formed within the shaft 115 and the tip 116, and extends from shaft opening 115' to tip opening 116'.

The liquid delivery device 110 further includes a control unit 118 and a first user interface 119, wherein the control unit 118 and the first user interface 119 are capable of exchanging electrical signals. The internal sensor 117 is capable of exchanging signals with the control unit 118. The control unit 118 and/or the first user interface 119 may be containable within the actuator 111, as shown in FIG. 4, or the control unit 118 and/or the first user interface 119 may be separate from the actuator 111 (not shown). For example, the control unit 118 and/or the first user interface 119 may be connectable to the cylinder 114, or the control unit 118 and/or the first user interface 119 may not be connectable to any other part of liquid delivery device 110. The first user interface 119 may be, but is not limited to being, an LED display.

While the system 100 of FIG. 4 is shown as having only one liquid delivery device 110, it is to be understood that the system 100 may include a plurality of liquid delivery devices 110. For example, the system 100 may include eight or twelve liquid delivery devices 110. When the system 100 includes a plurality of liquid delivery devices 110, each liquid delivery device 110 includes the piston 112 having the plunger 113, the cylinder 114 with shaft 115, the tip 116, and the one or more internal sensors 117. However, when the system 100 includes a plurality of liquid delivery devices 110, the system 100 may include a fewer number of actuators 11, control units 118 and/or first user interfaces 119, possibly just one of each. Alternatively, the system 100 may include one actuator 11, control unit 118, and/or first user interface 119 for each piston 112 having the plunger 113, cylinder 114 with shaft 115, and tip 116 included with the system 100.

The system 100 further includes a second user interface 130, a computing device 140, and an optional ambient condition device 150. The second user interface 130 may be, but is not limited to being, a monitor, keyboard and mouse in communication with the computing device 140. The optional ambient condition device 150 includes one or more external sensors 151. An exemplary external sensor 151 may be a capacitive relative humidity sensor or a resistive relative humidity sensor. A capacitive relative humidity sensor may be selected to operate over a wide humidity range and because it tends to be resistant to condensation. Further, a capacitive relative humidity sensor may be interchangeable with other such sensors if it is the laser-trimmed type. Resistive humidity sensors also tend to be interchangeable, but regardless of whether they are laser-trimmed, and are cost effective. Both capacitive and resistive relative humidity sensors are highly resistive to chemicals and physical wear. An example sensor considered suitable for the purpose of sensing external conditions is the Model DS1923 Humidity and Temperature Data-Logger iButton® available from Maxim Integrated Products, Inc. of Sunnyvale, Calif., which detects relative humidity and temperature external to the liquid delivery device 110. Other suitable external sensors may be used as is known by those of ordinary skill in the art. The computing device 140 is capable of exchanging signals with the liquid delivery device 110. The second user interface 130 is capable of exchanging signals with the computing device 140. The ambient condition device 150 is capable of exchanging signals with the control unit 118. It is to be understood that any of the noted devices may exchange signals with each other directly or indirectly, remotely, locally, and in a wired or wireless manner.

The computing device 140 may include computer-executable software which includes computer-readable signals tangibly embodied on computer-readable medium, where such signals define instructions for processing information obtained from the control unit 118, internal sensors 117 and/or ambient condition device 150. Such instructions may be written in any of a plurality of programming languages, for example, Java, XML Visual Basic, C, or C++, Fortran, Pascal, Eiffel, BASIC, COBOL, and the like, or any of a variety of combinations thereof. The computer-readable medium on which such instructions preferably reside is to be compatible with the central processing unit of the computing device 140.

When the system 100 is in operation, the piston 112 having the plunger 113 is movable in a linear direction toward and away from cylinder inner lower wall 114", through which opening 115' of the shaft 115 is formed. Movement of the piston 112 having the plunger 113 is effected by, and under control of, the actuator 111. As the piston 112 having the plunger 113 is moved away from shaft opening 115', space 120 increases in size and gas contained in the shaft 115 and tip 116 and, possibly, from outside the system 100, is drawn into space 120. When the piston 112 having the plunger 113 is moved away from the shaft opening 115', therefore, some gas contacts and flows by the internal sensor 117 in a direction toward plunger lower surface 113'. If the tip opening 116' is immersed in liquid as the plunger 113 is moved away from shaft opening 115', some of the liquid in which the tip opening 116' is immersed may be aspirated into the tip 116. Conversely, as the piston 112 having the plunger 113 is moved toward the shaft opening 115', space 120 decreases in size and some gas contained in space 120 may be forced into the shaft 115, where it then may contact and flow by the internal sensor 117, before entering the tip 116. Some gas entering the tip 116 may exit the liquid delivery device 110 through tip opening 116'. If liquid is contained within the tip 116 when the plunger 113 is moved toward the opening 115', some or all of the liquid may be dispensed from the tip 116 through tip opening 116'.

The internal sensor 117 may obtain information regarding the gas contained in space 120 and that information may be transmitted by the internal sensor 117 to the control unit 118. Likewise, when the optional ambient condition device 150 is included, the second sensor 151 of the ambient condition device 150 may obtain information regarding the ambient conditions outside the system 100, such as, for example, the temperature, relative humidity, barometric pressure of the ambient air outside the system 100, and the temperature of any liquid outside the system 100, and this information may be transmitted by the ambient condition device 150 to the control unit 118. In turn, some or all of the information received by the control unit 118 from the internal sensor 117 and/or the ambient condition device 150 optionally may be transmitted by the control unit 118 to the computing device 140. Information regarding the gas and/or ambient conditions received by either one or both of the control unit 118 and computing device 140 may be used by the control unit 118 and/or the computing device 140 to calculate one or more properties of the gas and/or ambient conditions according to one or more algorithms pre-programmed into the control unit 118 and/or the computing device 140. For example, based on the information received, the control unit 118 and/or the computing device 140 may calculate one or more of the volume, the mass, the pressure and the temperature of the gas, and may calculate one or more of the temperature, barometric pressure, and relative humidity of the ambient air surrounding the system 100. Further, the internal sensor 117 may be capable of obtaining information that may be used by the control unit 118 and/or the computing device 140 to calculate one or more properties of any gas in proximity to the internal sensor 117 when the plunger 113 is not being used to effect the flow of gas by the internal sensor 117, such as when the plunger 113 is in a resting state.

When the control unit 118 determines one or more properties of the gas and/or the ambient conditions, the control unit 118 and/or the computing device 140 may use all or some of this information to effect optimal adjustment of the performance of the liquid delivery device 110. One or more properties of the gas and/or ambient conditions determined by the control unit 118 and/or the computing device 140 may be displayed in a form understandable to an operator of the system 100 by the first user interface 119 and/or the second user interface 130. For example, if the control unit 118 and/or the computing device 140 calculate that the pressure of the gas is 960 mbar, the first user interface 119 and/or the second user interface 130 may display "960 mbar" as an icon. This would be helpful, for example, when the operator wishes to record that value for the purpose of making sure that the system 100 is performing consistently over time.

Alternatively, instead of automatically calculating one or more properties of the gas and/or ambient conditions without further human input, an operator of the system 100 may direct the control unit 118 and/or computing device 140 to calculate one or more properties of the gas and/or ambient conditions by interacting with the control unit 118 and/or computing device 140 through the first user interface 119 and/or the second user interface 130. For example, if the control unit 118 and/or the computing device 140 calculate the pressure of the gas as being 960 mbar, the operator then may enter a value or plurality of values representing one or more other properties of the gas and/or ambient conditions, e.g., the operator may enter 23.5° C. as being the temperature of the ambient air external to the liquid delivery device 110, and this value or plurality of values may be used by the control unit 118 and/or the computing device 140 in subsequent calculation steps. As another example, if the control unit 118 and/or the computing device 140 calculate the pressure of the gas, the operator may direct the control unit 118 and/or the computing device 140, via the first user interface 119 and/or the second user interface 130, to determine the pressure one or more times. This would be helpful, for example, when the operator believes that the first determined pressure value may have been inaccurately determined.

Calculated properties of the gas and/or ambient conditions also may be used in determining one or more properties of the particular liquid being aspirated into the tip 116. These one or more properties of the particular liquid being aspirated into the tip 116 then may be used to optimize the performance of the liquid delivery device 110. For example, when the liquid delivery device 110 has aspirated a particular liquid into the tip 116, the control unit 118 and/or computing device 140 may use information received from the internal sensor 117 to determine, for example, the pressure of the gas in space 120 as the liquid is being drawn into the tip 116. The control unit 118 and/or computing device 140 then may calculate the viscosity of the liquid, for example, by using this determined pressure value. In turn, using the determined viscosity of the liquid, the control unit 118 then may, for example, adjust the speed of the piston 112 having the plunger 113 within the cylinder 114, or the computing device 140 may signal the control unit 118 to do the same, to ensure that optimal aspiration of the liquid is achieved in subsequent operations.

As a more specific example of the operation of the system 100, the actuator 111 moves the plunger 113, via the piston 112, to a particular distance toward lower inner surface 114" of the cylinder 114, with gas being present in space 120. (This movement of the plunger 113 toward surface 114" causes some gas to be expelled from the space 120 through tip opening 116'.) The tip opening 116' is then immersed into a liquid sample. The actuator 111 moves the plunger 113 to a particular distance away from surface 114", and as a result of this movement, atmospheric pressure acting on the liquid sample forces some of the liquid into the tip 116, with flow of the liquid into the tip 116 continuing until pressure between the liquid sample and from within the space 120 equalizes, as sensed by the sensor 117 and communicated to the control unit 118 (either directly or via the computing device 140). The amount of liquid aspirated into the tip 116 is approximately equal to the volume of the gas displaced by the plunger 113 when it was moved away from surface 114". The control unit 118 then may direct the operator to keep tip opening 116' immersed in the liquid sample for a short period of time, such as approximately two seconds, for example, for a liquid sample of low viscosity, or for a longer period of time, such as about 33 seconds, for example, for a liquid sample of high viscosity, after the plunger 113 has stopped moving away from surface 114" to allow equilibrium to become established.

Continuing with this example, any liquid contained in the tip 116 after aspiration and achievement of equilibrium may be dispensed from the tip 116. It is anticipated that for most applications, liquid contained in the tip 116 will be dispensed from the tip 116 for the purpose of transferring that liquid from a first vessel to a second vessel. It is to be understood, however, that the liquid contained in the tip 116 may be dispensed from the tip 116 for any one of a variety of purposes which would be apparent to those of ordinary skill in the art. For example, the liquid contained in the tip 116 may be dispensed from the tip 116 for the purpose of spotting onto a solid substrate, such as a nylon membrane, for example, or in a titration application.

When liquid contained in the tip 116 is to be dispensed into a second vessel, the tip 116 may be moved from the first vessel to the second vessel, or the first vessel may be moved from the tip 116 and the second vessel may be moved to the tip 116. This movement may be effected manually by the operator or automatically by a device that is not part of the system 100. Further, when the liquid contained in the tip 116 is to be dispensed into a second vessel, the second vessel may be empty or it may contain liquid which may be of identical or different composition to the liquid contained in the tip 116. Regardless of how the tip 116 moves from the first vessel to the second vessel, the tip 116 may be positioned such that part of tip opening 116' contacts an inner surface of the second vessel, all of the opening 116' becomes immersed within, or flushly contacts the surface of, any liquid sample that may be contained in the second vessel, or none of the opening 116' contacts any part of the second vessel or any liquid sample contained in the second vessel.

Continuing with this example, once the tip 116 is positioned with respect to the second vessel, as directed by the control unit 118, the actuator 111 moves the plunger 113 toward surface 114" of the cylinder 114. This movement forces liquid contained in the tip 116 to be expelled from the tip 116 through its opening 116'. When the tip 116 is positioned near the surface of a liquid sample into which the liquid contained in the tip 116 is to be dispensed or is near the surface of the vessel onto which the liquid contained in the tip 116 is to be dispensed, surface tension may be created between the liquid in the tip 116 and the surface of the liquid sample or vessel. To sufficiently overcome the force of this tension such as to allow all of the liquid contained in the tip 116 to be expelled from the tip 116, the plunger 113 may be moved close to, and perhaps placed in contact with, surface 114".

Figure 5:
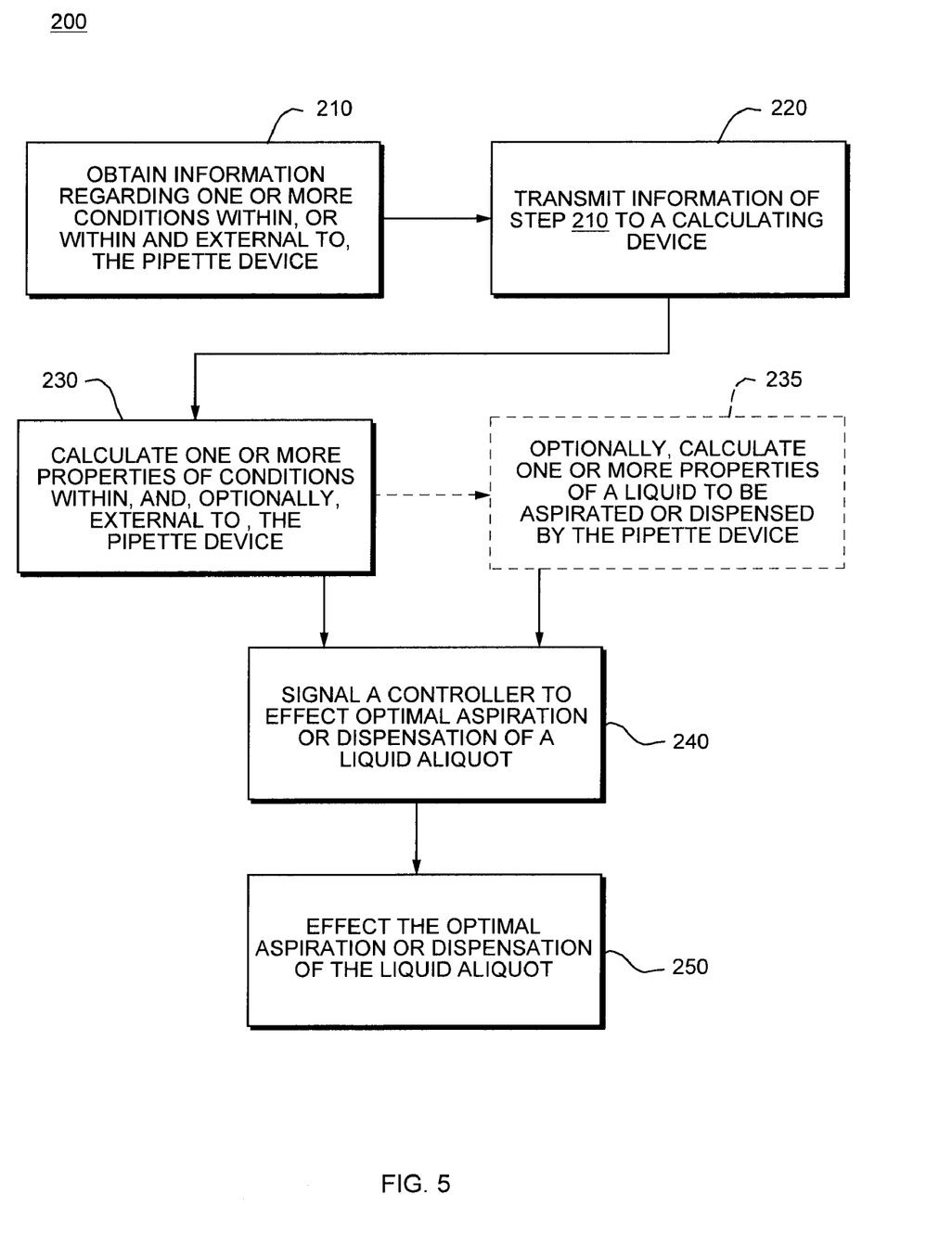
FIG. 5 is a flow diagram showing steps of a method of using the air displacement liquid delivery system of the present invention.

A method 200 of using the system 100 to optimally aspirate or dispense a liquid aliquot is generally presented in FIG. 5. In step 210, information regarding one or more conditions within and external to the liquid delivery device 110 is obtained. This may be achieved, for example, by the internal sensor 117, and/or the external sensor 151. (These conditions may be, for example, the temperature of the gas within the liquid delivery device 110 and the temperature of the air external to the liquid delivery device 110.) In step 220, information obtained in step 210 is transmitted to a calculating device. The calculating device may be, for example, the control unit 118 and/or the computing device 140. In step 230, the calculating device calculates one or more properties of conditions within the liquid delivery device 110 and external to the liquid delivery device 110. (For example, when the control unit 118 and/or the computing device 140 are used as the calculating device, either or both of the control unit 118 and/or the computing device 140 may calculate the temperature of the gas within the liquid delivery device 110 to be 26.6° C. and the temperature external to the liquid delivery device 110 to be 23.9° C.) In optional step 235, if any liquid was contained in the tip 116 of the liquid delivery device 110 during step 210, the calculating device may calculate one or more properties of the liquid. (For example, when the control unit 118 and/or the computing device 140 are used as the calculating device, either or both of the control unit 118 and/or the computing device 140 may calculate the temperature of the liquid to be 4.0° C.) In step 240, the calculating device signals a controller, such as, for example, control unit 118, to effect the optimal aspiration or dispensation of the liquid aliquot. In step 250, the controller effects optimal aspiration of the liquid aliquot.

In a first example of the method 200, the operator of the system 100 sets the desired aspiration volume via, for example, the second user interface 130, and the tip 116 is immersed into a source liquid from which an aliquot is to be aspirated. The piston 112 is moved from a default position to a position which is appropriate for the volume of the aliquot to be aspirated. (This position is referred to as the "set point position".) The internal sensor 117 then obtains information regarding the flow rate of the liquid into the tip 116 and corresponding decrease in pressure across the tip 116. Based upon this information regarding the flow rate and decrease in pressure, the control unit 118 determines the viscosity of the liquid. Depending on the viscosity of the liquid aliquot, the control unit 118 may continue moving the piston 112 (via the actuator 111) away from surface 114" in such a manner as to maintain a constant flow rate of the liquid into the tip 116. Further, the control unit 118 calculates the total volume of the liquid continuously as its being aspirated into the tip 116. As the calculated volume approaches the volume set by the operator, the piston 112 is moved via the actuator 111 back toward the set point position, with the piston 112 then reaching the set point position at essentially the same time the volume of the liquid that is actually aspirated into the tip 116 equals the volume set by the operator. The control unit 118 then determines when flow of liquid into the tip 116 has ceased. The stoppage of this flow represents the optimal time for the operator or system 100 to remove the tip 116 from the source vessel, which prevents any further evaporation or heat transfer. The tip 116 is then removed from the source liquid and placed within a second vessel. Once the tip 116 is within the second vessel, the piston 112 is returned to its default position. Return of the piston 112 to the default position causes all of the liquid that was aspirated into the tip 116 to be dispensed from the tip 116.

Figure 6:
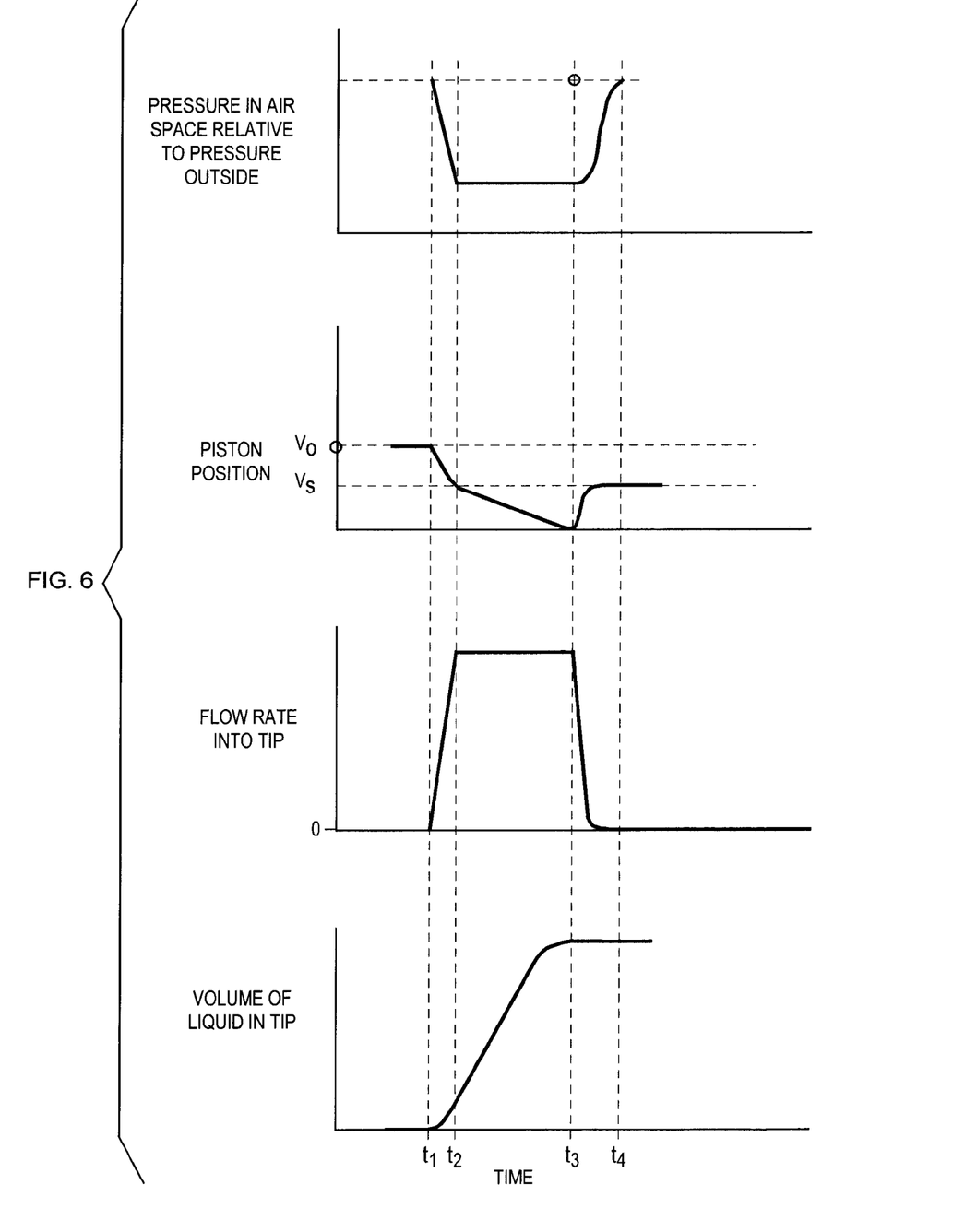
FIG. 6 is a series of graphs showing the change in air pressure within the liquid delivery device relative to pressure outside of the liquid delivery device, position of the piston, rate of flow of the liquid into the tip, and volume of liquid in the tip at various times in one example of the method of the present invention.

FIG. 6 shows a graphical illustration of the change in air pressure within the liquid delivery device 110 relative to pressure outside of the system 100, position of the piston 112, rate of flow of the liquid into the tip 116, and volume of liquid in the tip 116 at the time aspiration begins ($t_1$), the time that maximum flow rate of the liquid being aspirated is achieved ($t_2$), the time that the control unit 118 signals the piston 112 to move back toward the set point position ($t_3$), and the time that aspiration has ended ($t_4$). Specifically, at $t_1$ the piston 112 is at its default position ($V_0$), there is no liquid in the tip 116, the flow rate of the liquid is zero, and there is no difference in the pressure inside the liquid delivery device 110 with respect to the pressure outside the device 110. At $t_2$, the piston 112 reaches its set point position ($V_s$), causing the flow rate of the liquid into the tip 116 to be maximized and a small fraction of the set volume (as set by the system 100 operator) of the liquid to be aspirated into the tip 116. Further, at $t_2$, greatest discrepancy in the pressure inside the liquid delivery device 110 relative to the pressure outside the device 110 is first achieved. Between $t_2$ and $t_3$, the piston 112 steadily moves away from $V_s$ (and from $V_0$), with the flow rate of the liquid into the tip 116 to remain at maximum level as more and more of the set volume of the liquid is aspirated into the tip 116. (During this period, the pressure inside the liquid delivery device 110 relative to the pressure outside the device 110 remains constant.) At $t_3$, the piston begins to be returned to $V_s$, thereby causing the flow rate of the liquid into the tip 116 to begin to decrease toward zero and the volume of the liquid in the tip 116 to nearly reach the set volume. Further, at $t_3$, the pressure inside the liquid delivery device 110 relative to the pressure outside the system 100 begins to return to equilibrium. At $t_4$, the piston 112 has already been returned to $V_s$, the volume of the liquid in the tip 116 has already reached the set volume, the flow rate of the liquid into the tip 116 has diminished to zero, and the pressure inside the liquid delivery device 110 relative to the pressure outside the system 100 has returned to equilibrium.

Figure 7:
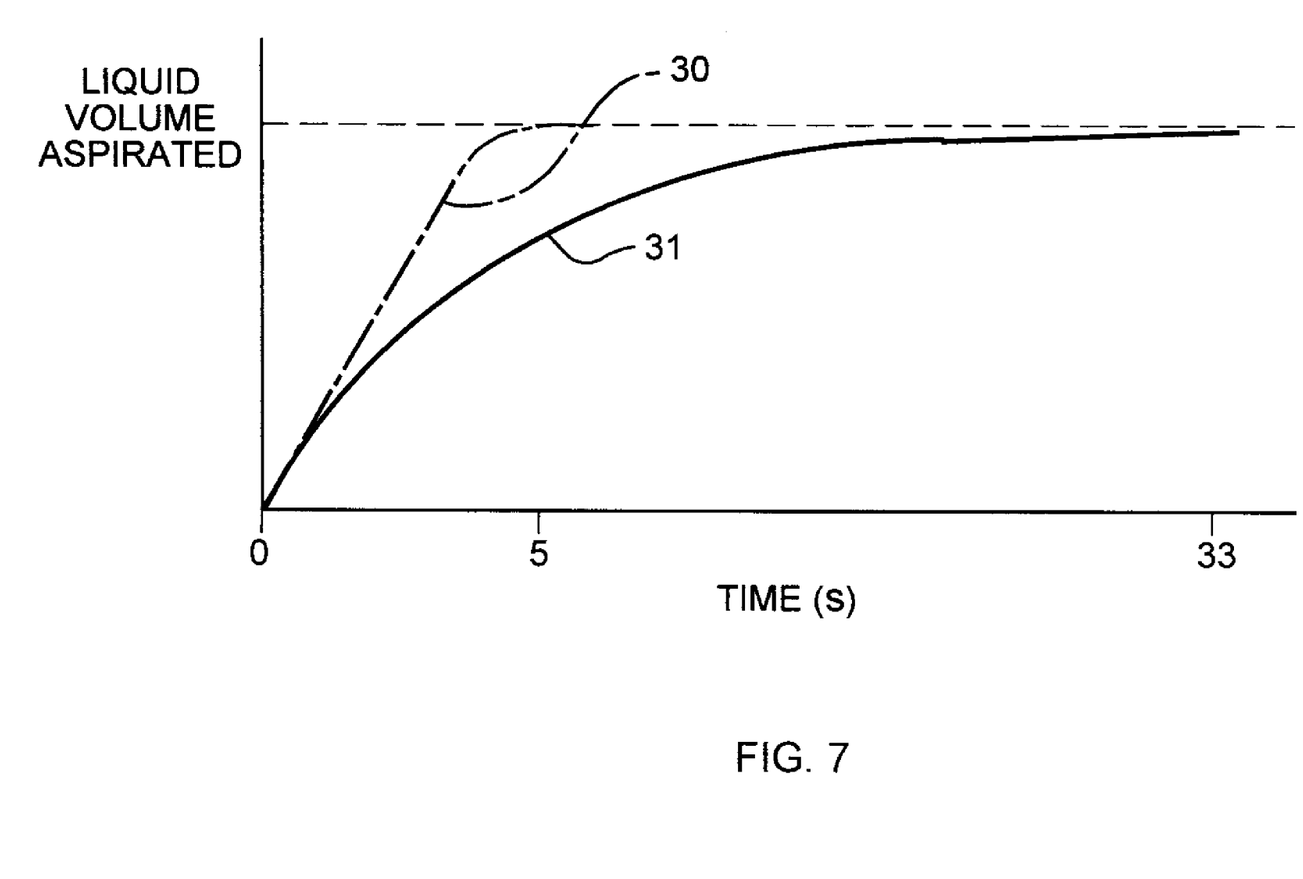
FIG. 7 is a graph showing a change in volume of a liquid actually aspirated by the present air displacement liquid delivery device of FIG. 4 as that volume approaches a desired volume, to which the present device of FIG. 4 was pre-adjusted to aspirate, over time.

In practice, the first example of the method would minimize the length of time that is required to aspirate an aliquot of liquid sample that is viscous. For example, FIG. 7 shows a graph comparing actual aspiration volumes of anhydrous glycerol versus time for the system 100 of the present invention and that of prior liquid delivery devices of FIGS. 1 and 2. The actual volume of anhydrous glycerol aspirated by the present system 100 is shown by dotted line 30 and the actual volume of anhydrous glycerol aspirated by the prior devices is shown as solid line 31. As shown in FIG. 7, the system 100 may fully aspirate a 100 μL sample of anhydrous glycerol at room temperature with the same tip 116 in as little as five seconds (reduced from 33 seconds from the prior devices) utilizing a "constant flow-rate" control algorithm. When viscous liquids are being aspirated, this drastically reduces the time required to complete a given aspiration/dispense cycle, operator fatigue, the possibility of error due to premature withdrawal, and the error due to evaporation or heat transfer. Other modes of operation that may be desirable to serve the same purpose, depending on the particular liquid or volume delivered, will be obvious to those of ordinary skill in the art.

In a second example of the method 200, the liquid delivery device 110 is preconditioned before being used to make a quantitative aspiration of a liquid with high vapor pressure. Generally, the exact procedure chosen for preconditioning of the liquid delivery device 110 will vary based on the nature of the liquid to be delivered and the nature of the liquid delivery device 110 itself. A plurality of varied preconditioning procedures may be storable by the computing device 140 and be accessible to the operator of the system 100 via second user interface 130. Therefore, if the operator is to aspirate an aliquot of methanol, for example, the operator may select a preprogrammed procedure that is specific to methanol at the second interface 130. One example of a preconditioning method that an operator may choose to have the system 100 perform has the following steps: (1) the operator selects the appropriate preconditioning procedure via second user interface 130; (2) the system 100 prepares for preconditioning by having the actuator 111 move the piston 112 away from surface 114" in a manner such that a small volume of ambient air is aspirated into the tip 116 through opening 116'; (3) the tip opening 116' is immersed into the methanol sample from which the liquid aliquot is to be aspirated; (4) the system 100 aspirates the greatest possible volume (based on the maximum capacity of the cylinder 114 and the tip 116) of the methanol aliquot as quickly as possible to create maximal turbulence, evaporation and mixing of the gas in volume 120; (5) while still holding the tip opening 116' immersed in the methanol sample, the system 100 expels most, but not all, of the methanol aliquot from the tip 116 back into the source vessel; (6) steps (1)-(5) are repeated five more times; and (7) the system 100 expels all of the methanol from the tip 116 and further expels a small amount of the gas contained in the tip 116 from the tip 116 through opening 116'. After following these steps, the system 100 is effectively preconditioned, and therefore is ready to make a quantitative aspiration of another aliquot of methanol.

In a third example of a method of using the system 100, the system 100 is used to make a quantitative aspiration from the liquid sample to which the system 100 was preconditioned in the second example described above. In this third example, the following steps are performed: (1) an aliquot of the methanol sample is aspirated into the tip 1116; (2) the volume of the aliquot is determined by the control unit 118 and/or computing device 140 by using information obtained by the internal sensor 117; (3) the operator or system 100 is signaled that the tip 116 is ready to be removed from the liquid sample and the tip 116 is removed from the liquid sample by the operator or the apparatus; (4) the sensor obtains information regarding change in pressure of the gas within the liquid delivery device 110 (this change in pressure results from the withdrawal of the tip 116 from the liquid sample in step 3); (5) using the information obtained in step 4, the control unit 118 and/or computing device 140 determines that the plunger 113 should be moved away from surface 114" to a particular distance and at a particular speed; and (6) the control unit 118 and/or computing device 140 directs the actuator 111 to effect this movement, thereby causing a gas bubble to form at the tip opening 116' (the gas bubble will prevent liquid from leaking from the tip 116 as the tip 116 is moved to a dispense location).

The examples of the method 200 described above are meant to illustrate only some of the possible ways by which the method 200 may be performed, and therefore the method 200 is not limited to being used according to these examples. Those of ordinary skill in the art would recognize the numerous ways, and variations thereof, that the method 200 may be performed.

It is to be understood that various modifications may be made to the system 100 without departing from the spirit and scope of the invention. Accordingly, other embodiments are within the scope of the claims appended hereto.

What is claimed is:

1. A method for optimizing the operation of a liquid delivery device in aspirating or dispensing a liquid, the method comprising the steps of:
    a. sensing one or more conditions within the liquid delivery device;
    b. sensing one or more conditions outside the liquid delivery device;
    c. calculating a rate of aspiration or dispensation of the liquid based on the sensed conditions inside and outside the liquid delivery device and one or more properties of the liquid;
    d. establishing a protocol for aspiration or dispensation of the liquid based on the one or more properties of the liquid and the one or more conditions inside and outside the liquid delivery device; and
    e. regulating the aspiration or dispensation of the liquid based on the calculated rate and the established protocol.

2. The method of claim 1 wherein the conditions sensed within the liquid delivery device include temperature, pressure, relative humidity, and flow of gas through or past one or more sensors.

3. The method of claim 1 wherein the conditions sensed outside the liquid delivery device include temperature, barometric pressure and relative humidity.

4. The method of claim 1, wherein the liquid is aspirated from a liquid source and the step of sensing one or more conditions outside the liquid delivery device includes the step of sensing the temperature of the liquid source.

5. The method of claim 1 wherein the liquid is aspirated from a liquid source and the step of calculating the rate includes the step of calculating the rate of removal of the liquid delivery device from the liquid source.

6. The method of claim 5 wherein the step of calculating the rate of removal includes the step of calculating an optimal removal time and the step of regulating includes the step of generating a signal to initiate removal of the liquid delivery device from the liquid source at the optimal removal time.

7. The method of claim 5 wherein the signal is transmitted to an operator to initiate manual removal of the liquid delivery device from the liquid source.

8. The method of claim 5 wherein the signal is transmitted to an automated control unit to initiate automated removal of the liquid delivery device from the liquid source.

9. The method of Claim 1 wherein the one or more properties of the liquid are selected from the group consisting of viscosity, vapor pressure, density, and surface tension.

10. A method for optimizing the operation of a liquid delivery device in aspirating a liquid from a liquid source, the method comprising the steps of:
   a. sensing one or more conditions within the liquid delivery device;
   b. calculating an optimal time to remove the liquid delivery device from the liquid source based on the sensed information inside the liquid delivery device; and
   c. generating a signal to initiate removal of the liquid delivery device from the liquid source at the optimal removal time.

11. The method of claim 10 wherein the signal is transmitted to an operator to initiate manual removal of the liquid delivery device from the liquid source.

12. The method of claim 10 wherein the signal is transmitted to an automated control unit to initiate automated removal of the liquid delivery device from the liquid source.

13. The method of claim 10 further comprising the steps of:
   a. including in the calculation of the optimal removal time one or more properties of the liquid; and
   b. establishing a protocol for aspiration of the liquid based on the one or more properties, and the one or more conditions on the inside of the liquid delivery device.

14. The method of claim 13 wherein the one or more properties are selected from the group consisting of viscosity, vapor pressure, density, contact angle between the liquid and the material of the tip, and surface tension.

15. The method of claim 10 further comprising the steps of:
   a. sensing one or more conditions outside the liquid delivery device; and
   b. including in the calculation of the optimal removal time the sensed conditions outside the liquid delivery device.

16. The method of claim 15 wherein one of the one or more sensed conditions outside the liquid delivery device is the temperature of the liquid source.

17. The method of claim 10 further comprising the step of preconditioning the liquid delivery device prior to the step of sensing, the step of preconditioning comprising the steps of:
   a. aspirating air into a tip of the liquid delivery device;
   b. immersing the tip in the liquid source;
   c. aspirating the liquid from the liquid source into the tip in a manner that causes turbulence, mixing and partial evaporation of the liquid in the tip;
   d. dispensing a portion of the liquid from the tip into the liquid source;
   e. repeating steps (a)-(d) one or more times;
   f. dispensing all of the liquid from the tip into the liquid source; and
   g. dispensing air from the tip.

18. The method of claim 17 wherein an operator of the liquid delivery device signals the liquid delivery device to perform one or more of steps (a)-(g) automatically.

19. The method of claim 18 wherein one or more of the steps (a)-(g) are storable by a computer program and the operator signals the computer program to signal the device to perform the one or more steps.

20. The method of claim 17 further comprising the steps of:
   a. after the air has been dispensed from the tip, aspirating liquid from the liquid source into the tip;
   b. sensing one or more conditions within the liquid delivery device after the air has been dispensed from the tip and the liquid has been aspirated from the liquid source into the tip;
   c. calculating the volume of the liquid in the tip based on the one or more conditions sensed after the air has been dispensed from the tip; and
   d. generating a signal to initiate removal of the liquid delivery device from the liquid source after the volume of the liquid has been calculated.

21. The method of claim 20 wherein the signal generated after the volume of the liquid has been calculated is transmitted to an operator to initiate manual removal of the liquid delivery device from the liquid source, or the signal is transmitted to an automated control unit to initiate automated removal of the liquid delivery device from the liquid source.

22. The method of claim 21 further comprising the steps of:
   a. removing the liquid delivery device from the liquid source after the signal generated after the volume of the liquid has been calculated has been transmitted to the operator or the control unit;
   b. sensing a change in pressure within the liquid delivery device;
   c. calculating a volume of air to be aspirated into the tip based on the one or more sensed conditions; and
   d. regulating the aspiration of the air into the tip based on the calculated volume of the air.

* * * * *